United States Patent [19]

Hunziker

[11] 3,959,282
[45] May 25, 1976

[54] 10-PIPERAZINO-4H-THIENO[2,3-C][1]BENZAZEPINES

[75] Inventor: Fritz Hunziker, Berne, Switzerland

[73] Assignee: Sandoz Ltd., Basel, Switzerland

[22] Filed: Mar. 21, 1975

[21] Appl. No.: 561,002

[30] Foreign Application Priority Data
Mar. 26, 1974 Switzerland.......................... 4189/74

[52] U.S. Cl.......................... 260/268 TR; 424/250; 260/239.3 T
[51] Int. Cl.²...................................... C07D 495/04
[58] Field of Search ............... 260/268 TR; 424/250

[56] References Cited
UNITED STATES PATENTS
3,842,082  10/1974  Hunziker ..................... 260/268 TR Primary Examiner—Alton D. Rollins
Assistant Examiner—Jose Tovar
Attorney, Agent, or Firm—Gerald D. Sharkin; Robert S. Honor; Thomas O. McGovern

[57] ABSTRACT

This invention provides new compounds of formula I,

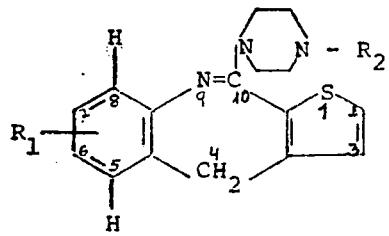

wherein
 $R_1$ is hydrogen, or alkyl, alkoxy or alkylthio of 1 to 4 carbon atoms, or trifluoromethyl, and
 $R_2$ is hydrogen, or alkyl, hydroxyalkyl or acetoxyalkyl, the alkyl moiety having at most 4 carbon atoms, or alkoxyalkyl having at most 6 carbon atoms, useful as antipsycholics and soporifics.

20 Claims, No Drawings

10-PIPERAZINO-4H-THIENO[2,3-C][1]BENZAZEPINES

The present invention relates to new 4H-thieno[2,3-c][1]benzazepine derivatives.

In accordance with the invention there are provided new compounds of formula I,

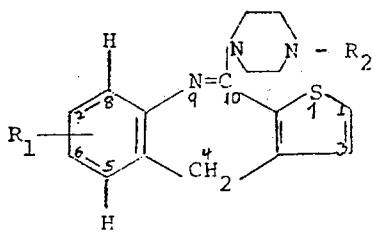

wherein $R_1$ is hydrogen, halogen, or alkyl, alkoxy or alkylthio of 1 to 4 carbon atoms, or trifluoromethyl, and $R_2$ is hydrogen, or alkyl, hydroxyalkyl or acetoxyalkyl, the alkyl moiety having at most 4 carbon atoms, or alkoxyalkyl having at most 6 carbon atoms.

When $R_1$ in formula I is halogen, halogen signifies fluorine, chlorine, bromine or iodine, especially chlorine or bromine, preferably, however, chlorine. When $R_1$ is an alkyl, alkoxy or alkylthio radical containing 1 to 4 carbon atoms, the alkyl radical may be straight chain or branched and may signify methyl, ethyl, or straight chain or branched propyl or butyl. When $R_2$ is an alkyl, hydroxyalkyl or alkoxyalkyl group, the alkyl or alkylene part may also be straight chain or branched. The alkyl group thereof contains 1 to 4 carbon atoms, the hydroxyalkyl group especially 2 to 4 carbon atoms. In the hydroxyalkyl group the hydroxyl group is preferably present in a β position. The substituent $R_1$ in formula I is exclusively either in position 6 or position 7.

Any carbon containing radical not particularly defined herein preferably has up to 5 carbon atoms.

Further, in accordance with the invention a compound of formula I may be obtained by a process comprising 1. reacting a compound of formula II,

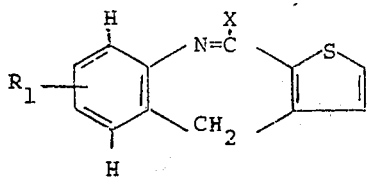

wherein $R_1$ is as defined above, and

X is a radical capable of being split off with the hydrogen of amines, with a compound of formula III,

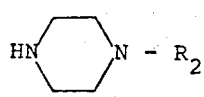

wherein $R_2$ is as defined above, or 2. reacting a compound of formula IV,

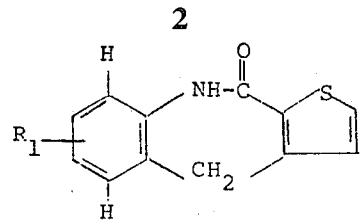

wherein $R_1$ is as defined above, with a metal amine complex consisting of a metal of the group IVb of the periodic system, or vanadium, and a compound of formula III, as defined above.

The process indicated in section (1) may be effected as follows:

The radical X may be bound to the carbon atom by a covalent or ionic bond and may signify an amino group which may optionally be substituted by one or two alkyl groups, a halogen atom, especially chlorine, the sulfhydryl group, an alkoxy or alkylthio group of 1 to 5 carbon atoms, e.g. the methoxy or methylthio group, an aralkylthio group which may optionally be activated by substituents, e.g. the p-nitrobenzylthio group or a tosyl group. There is conveniently present an inert organic solvent, e.g. xylene or dioxane. The reaction temperature is conveniently between 50° and 170°C, preferably between 100° and 140°C.

When the reactive group X is an amino group which may optionally be substituted, the reaction is conveniently effected in the presence of a catalytic amount of an acid, e.g. p-toluenesulphonic acid or sulphuric acid, or acid addition salts of the compounds of formula II are used as starting materials. However, it is also possible to use a salt having an acid reaction, such as ammonium chloride, as acid catalyst. An excess of compounds of formula III may also be used as reaction medium in place of a solvent.

The reaction of the invention is especially effected by heating the reaction mixture to the boil, for 2 to 6 hours. It is not absolutely necessary to use the compounds of formula II in isolated form.

The process indicated in section 2) may be effected as follows:

Compounds of formula IV are reacted with a metal amine complex, conveniently in the presence of an acid-binding agent. Acid-binding agents which may be used are tertiary amines, e.g. triethylamine, pyridine, dimethylaniline, or an excess of the compound of formula III. The portion of acid-binding agent calculated on 1 mol of metal amine complex is conveniently at least 1 mol (equivalent amount), preferably, however, 2 mols (twofold equivalent amount).

The reaction is conveniently effected in an organic solvent, e.g. an aromatic solvent such as toluene, a halogenated aromatic solvent such as chlorobenzene, a halogenated aliphatic solvent such as dichloroethane, or an ether such as anisole. The reaction temperature may be between room temperature and 150°C, preferably between 50° and 120°C.

The metal amine complex used for the reaction of the invention is obtained by reacting a halide, preferably the tetrachloride or tetrabromide, of a metal of the group IVb of the periodic system, or vanadium, with a compound of formula III, conveniently at a mol ratio of 1:4. The reaction is conveniently effected in the solvent subsequently used for the main reaction. The metal halide is used in the form of its soluble (mono- or di-)

etherate, preferably the anisole dietherate.

Of the metals included in the group IVb of the periodic system: titanium, zirconium and hafnium, it is preferred to use titanium and zirconium and especially titanium for this process.

The compounds of formula I obtained in accordance with the invention may be isolated in known manner, e.g. by precipitation from the reaction mixture, concentration of the reaction mixture by evaporation or salt formation. When the compounds of formula I are produced in accordance with the process of section (2), it is necessary, before isolating the compounds, to remove the metal portion present in the solution by precipitation by the addition of water. The resulting compounds of formula I may be purified in known manner, e.g. by recrystallization.

The compounds of formula II wherein X is halogen or alkoxy or sulfhydryl or alkylmercapto, used as starting materials in the process of section (1), may be obtained (a) by treating compounds of formula IV in known manner with a halogenating agent, e.g. a chlorinating agent such as phosphorus oxychloride or phosphorus pentachloride, preferably in the presence of catalytic amounts of dimethyl aniline or dimethyl formamide, or (b) by treating compounds of formula II wherein X is halogen, with an alkali metal alcoholate, or (c) by converting compounds of formula IV in known manner into the thiolactams, i.e. into compounds of formula II wherein X is sulfhydryl, or (d) by alkylating these thiolactams in known manner. Treatment of compounds of formula II wherein X is halogen, with ammonia or a lower mono- or dialkyl amine, yields compounds of formula II wherein X is an amino group which may optionally be mono- or dialkylated.

Those compounds of formula II wherein X is other than an amino group which may optionally be mono- or dialkylated, a halogen, alkoxy, sulfhydryl or alkylmercapto group, may be produced using known processes.

Compounds of formula IV may, for example, be obtained by ring closure of compounds of formula VI,

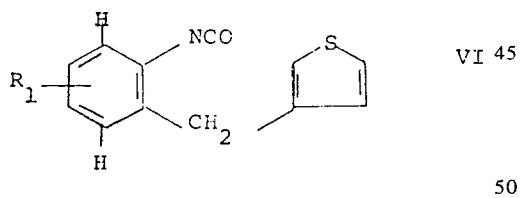

wherein $R_1$ is as defined above, in the presence of phosphorus oxychloride and phosphorus pentoxide, or preferably polyphosphoric acid.

Compounds of formula VI may, for example, be obtained by treating compounds of formula VII,

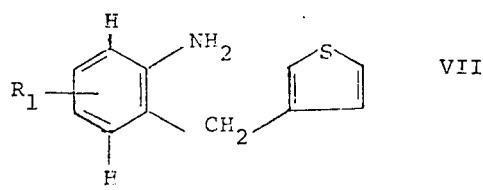

wherein $R_1$ is as defined above, with phosgene.

Compounds of formula VII may, for example, be obtained by reduction of compounds of formula VIII,

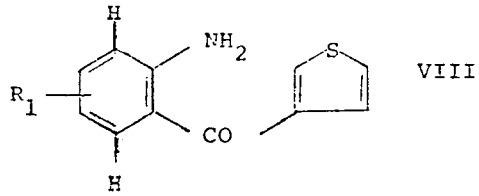

wherein $R_1$ is as defined above.

Compounds of formula VIII may be obtained by reacting 3-bromothiophene with n-butyl lithium in known manner, and allowing to react the resulting 3-lithiothiophene with a compound of formula IX,

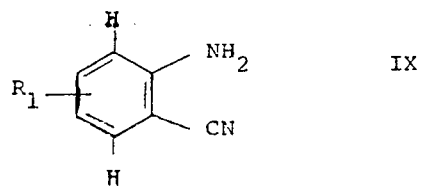

wherein $R_1$ is as defined above, in an inert organic solvent, e.g. ether/hexane, at a temperature between −75° and +30°C, and subjecting the resulting compound of formula X,

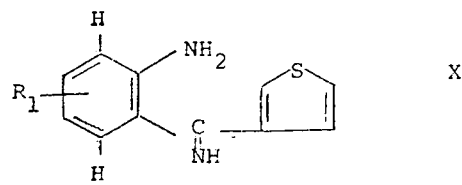

wherein $R_1$ is as defined above, to an acid hydrolysis with dilute hydrochloric acid at a temperature of 50° to 100°C.

The compounds of formula IV, used as starting materials in the process of section (2), may be produced as described above.

Free base forms of compounds of formula I may be converted into acid addition salt forms in conventional manner and vice versa. A suitable acid for salt formation is maleic or hydrochloric acid.

In the following non-limitative Examples all temperatures are indicated in degrees Centigrade, room temperature is between 20° and 30°C, and the vacuum usually employed is between 8 and 20 mm Hg, unless otherwise indicated.

EXAMPLE 1

10-(4-methyl-1-piperazinyl)-4H-thieno[2,3-c][1]benzazepine [process 1)]

3.25 g of 4,9-dihydro-10H-thieno[2,3-c][1]-benzazepin-10-one are heated to the boil at reflux for 3 hours together with 23 cc of phosphorus oxychloride and 0.9 cc of N,N-dimethylaniline. The reaction mixture is subsequently evaporated to dryness, and the residue is dried twice with xylene at 60°. The residue, containing 10-chloro-4H-thieno[2,3-c][1]benzazepine, is subsequently taken up in 16 cc of absolute dioxane, and 20 cc of N-methylpiperazine are added to the mixture. The reaction mixture is heated to the boil at reflux for 6 hours and is subsequently evaporated to dryness in a vacuum at 60°. The resulting residue is stirred with dilute acetic acid at 60° for 10 minutes, and the mixture is then filtered. The filtrate is clarified with charcoal and made alkaline with concentrated ammonia solution. A precipitate is obtained, which is taken up as suspension in ether. The ether phase is washed with water, dried over sodium sulphate and evaporated to dryness. The residue is clarified in a benzene solution on basic aluminium oxide. After removing the solvent by evaporation a residue is obtained, which is recrystallized from acetone/petroleum ether. The resulting 10-(4-methyl-1-piperazinyl)-4H-thieno[2,3-c][1]-benzazepine is obtained in the form of colourless grains having an M.P. of 175°–177°.

The 4,9-dihydro-10H-thieon[2,3-c][1]-benzazepin-10-one, used as starting material in the above process, is obtained as follows:

14.8 g of 3-(amino-benzoyl)thiophene, 23.8 g of solid potassium hydroxide and 19.6 g of hydrazine hydrate are heated to the boil at reflux in 180 cc of diethylene glycol for 3 hours. After diluting the reaction mixture with ice water, extraction is effected with ether. The ether phase is washed thrice with water, is dried with sodium sulphate and concentrated. 3-(2-amino-benzyl)thiophene is obtained in the form of a light yellow oil having a B.P. of 121°–123°/0.05 mm Hg.

46 cc of a 20 % solution of phosgene in toluene is added dropwise at −3° while stirring to a solution of 9.8 g of the product obtained above in 60 cc of toluene. The reaction mixture is subsequently allowed to warm to room temperature while passing through a stream of phosgene, and heating is subsequently effected to the boil at reflux for half an hour. After expelling the excess phosgene by the introduction of a stream of nitrogen, the reaction mixture is concentrated in a vacuum and the residue is distilled. 3-(2-isocyanato-benzyl)thiophene is obtained as mobile oil having a B.P. of 105°–106°/0.02 mm Hg.

10.5 g of 3-(2-isocyanato-benzyl)thiophene are heated to 110° together with 105 g of polyphosphoric acid while stirring for 1 hour. The reaction mixture is then made alkaline with concentrated ammonia solution while cooling with ice internally and externally, and the resulting precipitate is filtered off. This is washed with water and after drying is crystallized from acetone while treating with charcoal. 4,9-dihydro-10H-thieno[2,3-c][1]benzazepin-10-one, having an M.P. of 236°–238°, is obtained.

The 3-(2-amino-benzoyl)thiophene, used above as starting material, is obtained in known manner by reaction of 3-lithiothiophene (prepared in situ from 3-bromothiophene and n-butyl lithium) and o-aminobenzonitrile, and subsequent acid hydrolysis of the resulting ketimine.

EXAMPLE 2

10-(4-methyl-1-piperazinyl)-4H-thieno[2,3-c][1]benzazepine [process 2)]

2.2 cc (0.02 mols) of titanium tetrachloride and 4.35 cc of anisole (0.04 mols) are mixed with 40.5 cc of toluene, whereby a red solution is obtained. A solution of 8.91 cc (0.08 mols) of N-methylpiperazine in 4.9 cc of toluene is subsequently added within 10 minutes while stirring and cooling, whereby a green insoluble complex results. 4.3 g (0.02 mols) of 4,9-dihydro-10H-thieno[2,3-c][1]benzazepin-10-one and a further 4.5 cc (approximately 0.04 mols) of N-methylpiperazine are subsequently added. The mixture is then boiled at reflux while stirring for 3 hours.

After cooling slightly, 3 cc of water are added, and after stirring for some time, the resulting precipitate is filtered with suction. The filter residue is washed with methanol. The filtrate is then evaporated to dryness in a vacuum and is stirred with dilute acetic acid while heating slightly to 60° for 15 minutes. After removing the insoluble material by filtration and clarifying with charcoal, the basic portions are precipitated with concentrated aqueous ammonia solution and are taken up in ether. The ether phase is washed thrice with water, dried with sodium sulphate and concentrated. The residue is clarified in an ether solution on basic aluminium oxide. After crystallization from acetone/petroleum ether, 10-(4-methyl-1-piperazinyl)-4H-thieno-[2,3-c][1]benzazepine is obtained in the form of practically colourless grains having an M.P. of 176°–178°.

The following compounds of formula I are obtained using the processes described in the preceding Examples 1 and 2 and the corresponding starting materials: (certain of the compounds exist in more than one crystal modification)

| Ex. | $R_1$ | $R_2$ | M.P. |
|---|---|---|---|
| 3 | 7-Cl | —$CH_3$ | |
| 4 | 6-Br | —H | |
| 5 | 7-$CH_3$ | —$CH_2$—$CH_2$—OH | |
| 6 | 7-$OCH_3$ | —$CH_3$ | |
| 7 | 6-$SCH_3$ | —H | |
| 8 | H | —$CH_2$—$CH_2$—O—$\overset{\overset{O}{\|\|}}{C}$—$CH_3$ | |
| 9 | H | —$CH_2$—$CH_2$—OH | 80–90°/110–118° |
| 10 | 7-Cl | H | |
| 11 | 7-Cl | —$CH_2$—$CH_2$—OH | |
| 12 | H | H | 71–73°/130–133° |
| 13 | 7-$CF_3$ | —$CH_2$—$CH_2$—$OCH_3$ | |

The compounds of formula I are furthermore useful as antipsychotic and sedative agents, as indicated for example by an inhibition of locomotor activity in mice on p.o. administration of from about 0.1 to about 5 mg/kg animal body weight of the compounds (method of Caviezel and Baillod, described in Pharm. Acta Helv. 33, 465–484 [1958]) and furthermore by an inhibition of the electroencephalographic waking reaction in rabbits (method of Stille et al., described in Int.

J. Neuropharmacology 4, 375–391 [1965]), on i.v. administration of from about 0.5 to about 5 mg/kg animal body weight of the compounds.

For this use the dosage will, of course, vary depending on the compound employed, mode of administration and treatment desired. However, in general, satisfactory results are obtained when administered at a daily dosage of from about 0.1 mg to about 10 mg per kg animal body weight, conveniently given in divided doses 2 to 4 times a day or in sustained release form. For the larger mammals, the total daily dosage is in the range from about 5 to about 500 mg, and dosage forms suitable for oral administration comprise from about 1 mg to about 250 mg of the compounds admixed with a solid or liquid pharmaceutical carrier or diluent.

In particular, the compounds of formula I wherein $R_1$ is hydrogen are useful as soporifics, e.g. for inducing profound sleep, as indicated by a significant increase in the deep sleep phase (method of Stille et al., described in Psychopharmacologia 28, 325–337 [1973]), on i.v. administration of from about 0.1 to about 10 mg/kg animal body weight of the compounds.

For the above mentioned use the dosage will, of course, vary depending on the compound employed, mode of administration and therapy desired. However, in general, satisfactory results are obtained when administered at a daily dosage of from 0.1 mg to about 10 mg per kg animal body weight, conveniently given in divided doses 2 to 4 times a day or in sustained release form. For the larger mammal, the total daily dosage is in the range from about 5 to about 100 mg, and dosage forms suitable for oral administration comprise from about 1 mg to about 50 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent.

Such compositions may formulated in conventional manner to be in the form of, for example, a solution or a tablet.

Representative acid addition salt forms include organic acid salt forms such as the hydrogen maleate, fumarate, tartrate and methane sulphonate and mineral acid salt forms such as the hydrochloride, hydrobromide and sulphate.

The preferred compounds of formula I are those wherein $R_1$ is hydrogen or halogen, especially chlorine, and $R_2$ is hydrogen or methyl. When $R_1$ is halogen, especially chlorine, the 7 position is preferred.

The specially preferred compounds of the invention are 10-(4-methyl-1-piperazinyl)-4H-thieno-[2,3-c][1]benzazepine and 7-chloro-10-(4-methyl-1-piperazinyl)-4H-thieno[2,3-c][1]benzazepine.

In a group of compounds $R_1$ is hydrogen, halogen, alkyl, alkoxy or alkylthio.

I claim:
1. A compound of formula I, where
$R_1$ is hydrogen, halogen, or alkyl, alkoxy or alkylthio of 1 to 4 carbon atoms, or trifluoromethyl, and
$R_2$ is hydrogen, or alkyl, hydroxyalkyl or acetoxyalkyl, the alkyl moiety having at most 4 carbon atoms, or alkoxyalkyl having at most 6 carbon atoms, or a pharmaceutically acceptable acid addition salt thereof.

2. A method of treating psychoses in animals, which comprises administering to an animal in need of such treatment a therapeutically effective amount of a compound of claim 1.

3. A method of inducing sleep in animals, which comprises administering to an animal in need of such treatment a therapeutically effective amount of a compound of claim 1.

4. A pharmaceutical composition consisting essentially of a compound of claim 1 in association with a pharmaceutical carrier or diluent.

5. A compound of claim 1, wherein $R_1$ is hydrogen.

6. A compound of claim 1, wherein $R_1$ is halogen.

7. A compound of claim 1, wherein $R_2$ is hydrogen or methyl.

8. A compound of claim 1 wherein $R_1$ is hydrogen, halogen, alkyl, alkylthio or alkoxy.

9. The compound of claim 1 which is 10-(4-methyl-1-piperazinyl)-4H-thieno[2,3-c][1]benzazepine.

10. The compound of claim 1 wherein $R_1$ and $R_2$ respectively are 7—Cl, —CH$_3$.

11. The compound of claim 1 wherein $R_1$ and $R_2$ respectively are 6-Br, —H.

12. The compound of claim 1 wherein $R_1$ and $R_2$ respectively are 7-CH$_3$, —CH$_2$—CH$_2$—OH.

13. The compound of claim 1 wherein $R_1$ and $R_2$ respectively are 7-OCH$_3$, —CH$_3$.

14. The compound of claim 1 wherein $R_1$ and $R_2$ respectively are 6-SCH$_3$, —H.

15. The compound of claim 1 wherein $R_1$ and $R_2$ respectively are H, $$-CH_2-CH_2-O-\overset{O}{\underset{\|}{C}}-CH_3.$$

16. The compound of claim 1 wherein $R_1$ and $R_2$ respectively are H, —CH$_2$—CH$_2$—OH.

17. The compound of claim 1 wherein $R_1$ and $R_2$ respectively are 7—Cl, H.

18. The compound of claim 1 wherein $R_1$ and $R_2$ respectively are 7-Cl, —CH$_2$—CH$_2$—OH.

19. The compound of claim 1 wherein $R_1$ and $R_2$ respectively are H, H.

20. The compound of claim 1 wherein $R_1$ and $R_2$ respectively are 7—CF$_3$, —CH$_2$—CH$_2$—OCH$_3$.

* * * * *